United States Patent
Potechin et al.

(10) Patent No.: US 9,700,494 B2
(45) Date of Patent: Jul. 11, 2017

(54) FOAMING CLEANSER

(75) Inventors: Kathy Potechin, Short Hills, NJ (US); Christine Boyke, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/814,803

(22) PCT Filed: Aug. 11, 2010

(86) PCT No.: PCT/US2010/045125
§ 371 (c)(1),
(2), (4) Date: Feb. 7, 2013

(87) PCT Pub. No.: WO2012/021130
PCT Pub. Date: Feb. 16, 2012

(65) Prior Publication Data
US 2013/0137619 A1    May 30, 2013

(51) Int. Cl.

| | | |
|---|---|---|
| *C11D 1/02* | (2006.01) | |
| *C11D 1/88* | (2006.01) | |
| *C11D 1/94* | (2006.01) | |
| *A61K 8/39* | (2006.01) | |
| *A61K 8/44* | (2006.01) | |
| *A61Q 1/00* | (2006.01) | |
| *A61Q 19/10* | (2006.01) | |
| *A61K 8/04* | (2006.01) | |
| *A61K 8/34* | (2006.01) | |
| *A61K 8/46* | (2006.01) | |
| *A61K 8/86* | (2006.01) | |
| *A61K 8/92* | (2006.01) | |
| *C11D 1/74* | (2006.01) | |
| *C11D 3/20* | (2006.01) | |
| *C11D 17/08* | (2006.01) | |

(52) U.S. Cl.
CPC .............. *A61K 8/046* (2013.01); *A61K 8/345* (2013.01); *A61K 8/39* (2013.01); *A61K 8/44* (2013.01); *A61K 8/463* (2013.01); *A61K 8/86* (2013.01); *A61K 8/922* (2013.01); *A61Q 19/10* (2013.01); *C11D 1/74* (2013.01); *C11D 3/2065* (2013.01); *C11D 3/2093* (2013.01); *C11D 17/08* (2013.01)

(58) Field of Classification Search
CPC .... C11D 1/02; C11D 1/88; C11D 1/94; C11D 3/2065; C11D 3/2093; A61K 8/046; A61K 8/345; A61K 8/39; A61K 8/44; A61K 8/463; A61K 8/922; A61Q 1/00; A61Q 19/10
USPC ....... 510/124, 125, 127, 138, 159, 421, 426, 510/432, 433, 437, 490, 491, 492; 424/70.21, 70.22
See application file for complete search history.

(56) References Cited

U.S. PATENT DOCUMENTS

2007/0048235 A1    3/2007  Harmalker et al.

FOREIGN PATENT DOCUMENTS

| EP | 1964832 | 9/2008 | |
|---|---|---|---|
| RU | 2179844 | 2/2002 | |
| WO | WO 94/17166 | 8/1994 | |
| WO | WO 03/078558 | * 9/2003 | ............... C11D 1/02 |

OTHER PUBLICATIONS

Dr. Brandt Laser Lightning Foaming Cleanser, http://www.dermstore.com/product_Laser+Lightning+Foaming+Cleanser_13375.htm, retrieved from the Internet on Jun. 9, 2010.
Korres Natural Products Thyme & Sage Facial Gel Cleanser, sold in US circa Apr. 16, 2008, listed in Mintel Global New Product Database.
Korres Wild Rose Regiment Kit, http://www.sephora.com/browse/product.jhtml?id=P202939, retrieved from the Internet on Jun. 9, 2010.
Nutrimetrics Awakening Shower Crème, sold in Australia circa Dec. 17, 2009, listed in Mintel Global New Product Database.
Tegosoft GC and Tegosoft GMC 6 Technical Datasheet from Evonik Industries, Feb. 2008.
Watsons Active Bodycare Travel Pack, sold in China circa Nov. 2, 2006, listed in Mintel Global New Product Database.
International Search Report & Written Opinion issued for corresponding International Application No. PCT/US2010/045125, mailed Apr. 27, 2011.

* cited by examiner

*Primary Examiner* — Brian P Mruk

(57) ABSTRACT

An aqueous, foamable composition comprising castor oil maleate, PEG-7 glyceryl cocoate, glycerin, surfactant, and optionally PEG-6 caprylic/capric glycerides. The composition is useful as a foaming cleanser that dispenses a foam that has enhanced skin feel and optionally increased foam stand up so that it is less runny and messy.

18 Claims, No Drawings

FOAMING CLEANSER

BACKGROUND

Foaming hand soaps are cleansers that typically have a very low viscosity so that they can be dispensed through a foaming dispenser to deliver a foamed cleanser to a user. Typically, the foam does not stand up as a foam for a significant period of time. As the foam breaks, it can become runny and messy. It would be desirable to provide a foaming cleanser with increased foam stand up to improve the runniness and messiness of the foam. It would also be desirable to provide a foaming cleanser with enhanced skin feel properties.

SUMMARY

An aqueous, foamable composition comprising 0.1 to 1% by weight of the composition castor oil maleate, 0.05 to 0.3% by weight of the composition PEG-7 glyceryl cocoate, 0.5 to 6% by weight of the composition glycerin, surfactant, and water, wherein the glycerin is present in an amount that is greater than any of the castor oil maleate or the PEG-7 glyceryl cocoate, and the composition has a viscosity of 1 to 100 mPas (cps). The composition can provide an enhanced skin feel.

In another embodiment, the composition can further include 0.05 to 1% by weight of the composition PEG-6 caprylic/capric glycerides. This composition can provide foam stand up, and is less runny and messy to use.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The composition includes castor oil maleate, PEG-7 glyceryl cocoate, glycerin, surfactant, water, and optionally PEG-6 caprylic/capric glycerides.

Castor oil maleate (castoryl maleate) is present in the composition in an amount of 0.1 to 1% by weight of the composition. In one embodiment, the amount is about 0.3 to 0.5% by weight. In another embodiment, the amount is 0.5% by weight. Castor oil maleate is available as Ceraphyl™ RMT from ISP Corp.

PEG-7 glyceryl cocoate is present in the composition in an amount of 0.05 to 0.5% by weight of the composition. In one embodiment, the amount is 0.2% by weight. PEG-7 glyceryl cocoate is available from Cognis as Cetiol™ HE.

Glycerin is present in the composition in an amount of 0.5 to 6% by weight of the composition. The glycerin is present in an amount that is greater than any of the castor oil maleate, PEG-7 glyceryl cocoate, or the PEG-6 caprylic/capric glycerides. In one embodiment, the glycerin is present at about 3.4% by weight. While glycerin may have been included in foaming cleansers, typically the level has been low, generally close to 0.1 weight % or less. As glycerin level is increased, the expectation is that foaming would decrease, and in particular when the level of glycerin is above 3 weight %.

When included in certain embodiments, PEG-6 caprylic/capric glycerides is present in the composition in an amount of 0.05 to 1% by weight of the composition. In one embodiment, the amount is about 0.5% by weight. PEG-6 caprylic/capric glycerides is available from Croda as Glycerox™ 767.

Optionally, the composition can contain PEG-120 methyl glucose dioleate. In one embodiment, the amount of PEG-120 methyl glucose dioleate is 0.01 to 0.5% by weight of the composition, and in another embodiment the amount is 0.15% by weight. PEG-120 methyl glucose dioleate is available from Lubrizol Advanced Materials as Glucamate™ DOE-120 thickener. The inclusion of PEG-120 methyl glucose dioleate can further increase the foam stand up and skin feel properties.

The composition contains at least one surfactant. The surfactants can be any anionic, nonionic, cationic, amphoteric, or zwitterionic surfactant. In one embodiment, the surfactant comprises sodium lauryl ether (laureth) sulfate. In certain embodiments, the average number of ethylene oxide moieties per mole in the laureth sulfate is about 2 to about 8. In one embodiment, the average number is about 2. In another embodiment, the surfactant further comprises cocoamidopropyl betaine.

The surfactant can be present in an amount of 1 to 40% by weight of the composition. In other embodiments, the amount of surfactant is 1 to 30, 1 to 20, 5 to 20, 10 to 20, 10 to 15, or 15 to 20% by weight of the composition.

In one embodiment, the surfactant comprises sodium lauryl ether sulfate that is present in an amount of 5 to 10% by weight. In another embodiment, the amount is 7 to 8% by weight.

In another embodiment, the surfactant comprises a combination of sodium lauryl ether sulfate and cocoamidopropyl betaine. The amounts of sodium lauryl ether sulfate in this combination are the same as listed above, and the amount of cocoamidopropyl betaine is 5 to 10 or 5.5 to 6.5% by weight of the composition. In one embodiment, the surfactant comprises about 7.6% by weight sodium lauryl ether sulfate and about 6% by weight cocoamidopropyl betaine.

The viscosity of the composition in this specification and in the claims is 1 to 100 mPas (cps) as measured on a Brookfield DVII viscometer with spindle 3 at 100 rpm at 25° C. This allows the composition to be dispensed through a foaming dispenser and generate a foam. A foaming dispenser is any dispenser that intakes a liquid composition and then dispenses the composition as a foam.

When the PEG-6 caprylic/capric glycerides are included in the composition, the foam generated by this composition has more stand up and is less runny and messy to use. The combination of the castor oil maleate, PEG-7 glyceryl cocoate, PEG-6 caprylic/capric glycerides, and glycerin provide the increased stand up and a greater skin feel after the composition is used. The composition can be a foaming hand soap or a foaming body wash/shower gel.

In some embodiments the pH of the composition is 2 to 9. In one embodiment, the pH of the composition is 3 to 7. In other embodiments, the pH of the composition is 4 to 6. In another embodiment the pH of the composition is 6 to 8. The pH is measured at 25° C.

Additionally, the composition can contain any other materials that can be included in a cleansing composition.

Examples of additional surfactants and other materials can be found in United States Patent Publication No. 2007/0048235.

The compositions can be made by mixing of the materials.

SPECIFIC EMBODIMENTS

The invention is further described in the following examples. The examples are merely illustrative and do not in any way limit the scope of the invention as described and claimed.

The following inventive composition and comparative control are prepared using the procedure that follows. The amounts are weight % of the as supplied material.

| Material | Example 1 | Control |
|---|---|---|
| Water | Q.S. | Q.S. |
| Sodium lauryl ether sulfate (2EO) (70%) | 10.9 | 10.9 |
| Preservative | 0.7 | 0.7 |
| Cocoamidopropyl betaine | 6 | 6 |
| Castor oil maleate (Ceraphyl™ RMT) | 0.3 | 0 |
| Glycerin | 3.4 | 0 |
| PEG-6 caprylic/capric glycerides (Glycerox™ 767) | 0.5 | 0 |
| PEG-7 Glyceryl Cocoate (Cetiol™ HE) | 0.2 | 0.01 |
| Tetrasodium EDTA (39%) | 0.26 | 0.26 |
| PEG-120 Methyl Glucose Dioleate (Glucamate™ DOE-120 thickener) | 0.15 | 0.15 |
| Citric acid solution | 0.055 | 0.055 |
| Fragrance | 0.2-0.35 | 0.2-0.35 |
| color | 0.0001-0.0005 | 0.0001-0.0005 |

Castor oil maleate Premix—Ceraphyl™ RMT castor oil maleate is added to a beaker containing cocoamidopropyl betaine and mixed at high speed until fully incorporated and liquid is clear. Glycerin is added to the batch and mixed until homogeneous. Preservative (DMDM hydantoin) is then added to the batch and mixed until homogeneous.

DOE-120 Premix—Add water to beaker and heat to 35-50° C. Add PEG-120 Methyl Glucose Dioleate to beaker and mix at high speed until fully dissolved. Turn off heat. Once temperature is below 40° C., add preservative (DMDM Hydantoin) and mix until fully incorporated.

Add water to a vessel equipped with center turbine agitation and heat to 50° C. Once at 50° C., slowly add Sodium Lauryl Ether Sulfate to water while mixing at medium speed. Once all of the Sodium lauryl ether sulfate is dissolved, turn off heat and begin cooling the batch. When the temperature is below 40° C., add preservative (DMDM Hydantoin) and mix until homogeneous. Cocoamidopropyl betaine and glycerin are added to the batch in succession mixing until homogeneous in between components. Castor oil maleate premix (see above) is added to the batch slowly at a high speed and mixed until fully incorporated and batch is clear. Tetrasodium EDTA solution, PEG-6, DOE-120 premix (see above), PEG-7, fragrance and color are added in succession to the batch mixing until homogeneous in between components. pH and viscosity are measured and adjusted if necessary.

The study is a sequential monadic design whereby each subject evaluates test products over the course of the study. A total of 52 participants who regularly wash their hands and are not averse to using a foaming soap are recruited and selected to participate in the study.

Each subject washes with each test product once per test session. Subjects are asked to wash their hands twice per day (once in the AM, once in the PM) with the product and evaluate one test product per session. Subjects dispense the product using their normal habits, answer some questions related to dispensing, and then wash their hands with the product as normal and evaluate the product on a series of questions. Each subject evaluates all products in a balanced/randomized order of presentation over the course of the test sessions.

The following tables list the ratings provided by the 52 participants to questions about the products.

How much did you like or dislike this product?

| Rating | Example 1 | Control |
|---|---|---|
| 9: Like Extremely | 21.2% | 1.9% |
| 8: Like Very Much | 23.1% | 17.3% |
| 7: Like Moderately | 32.7% | 26.9% |
| 6: Like Slightly | 9.6% | 15.4% |
| 5: Neither Like nor Dislike | 7.7% | 7.7% |
| 4: Dislike Slightly | 5.8% | 9.6% |
| 3: Dislike Moderately | 0.0% | 17.3% |
| 2: Dislike Very Much | 0.0% | 3.8% |
| 1: Dislike Extremely | 0.0% | 0.0% |

How would you rate the consistency of the foam as you dispensed it?

| Rating | Example 1 | Control |
|---|---|---|
| 5: Much too thick | 0.0% | 0.0% |
| 4: Somewhat too thick | 11.5% | 3.8% |
| 3: Just about right | 84.6% | 40.4% |
| 2: Somewhat too thin | 3.8% | 46.2% |
| 1: Much too thin | 0.0% | 9.6% |

Consistency of the Foam (Just about Right): Example 1 has significantly more people rating the amount of foam as just about right versus Control (40%).

Has an appealing foam texture?

| Rating | Example 1 | Control |
|---|---|---|
| 5: Describes completely | 26.9% | 9.6% |
| 4: Describes very well | 51.9% | 34.6% |
| 3: Describes somewhat | 13.5% | 36.5% |
| 2: Does not describe very well | 5.8% | 17.3% |
| 1: Does not describe well at all | 1.9% | 1.9% |

Appealing foam texture: Example 1 has a significantly more appealing foam texture versus Control.

Is not messy to use?

| Rating | Example 1 | Control |
|---|---|---|
| 5: Describes completely | 44.2% | 19.2% |
| 4: Describes very well | 38.5% | 34.6% |
| 3: Describes somewhat | 15.4% | 28.8% |
| 2: Does not describe very well | 1.9% | 11.5% |
| 1: Does not describe well at all | 0.0% | 5.8% |

Example 1 was significantly more preferred for overall liking as compared to Control. Also, Example 1 is significantly less messy to use compared to Control.

What is claimed is:

1. An aqueous, foamable composition comprising:
   a) 0.1 to 1% by weight of the composition castor oil maleate,
   b) 0.05 to 0.3% by weight of the composition PEG-7 glyceryl cocoate,
   c) 0.5 to 6% by weight of the composition glycerin,
   d) surfactant, and
   e) 0.05 to 1% by weight of the composition PEG-6 caprylic/capric glycerides,
   wherein the glycerin is present in an amount that is greater than any of the castor oil maleate or PEG-7 glyceryl cocoate, and
   the composition has a viscosity of 1 to 100 mPas (cps).

2. The composition of claim 1 further comprising PEG-120 methyl glucose dioleate.

3. The composition of claim 2, wherein the PEG-120 methyl glucose dioleate is present in an amount of 0.01 to 0.5% by weight of the composition.

4. The composition of claim 1, wherein the surfactant comprises sodium lauryl ether sulfate and cocoamidopropyl betaine.

5. The composition of claim 4, wherein the sodium lauryl ether sulfate has an average of about 2 ethylene oxide moieties per mole.

6. The composition of claim 1, wherein the castor oil maleate is present at about 0.5% by weight, the PEG-7 glyceryl cocoate is present at about 0.2% by weight, and the glycerin is present at about 3.4% by weight.

7. The composition of claim 1, wherein the PEG-6 caprylic/capric glycerides is present at about 0.5% by weight.

8. The composition of claim 1, wherein glycerin is present in an amount of 3 to 6% by weight.

9. An aqueous, foamable composition comprising:
   a) castor oil maleate in an amount of 0.1 to 1% by weight of the composition,
   b) glycerin in an amount of 0.5 to 6% by weight of the composition,
   c) surfactant, and
   d) PEG-6 caprylic/capric glycerides in an amount of 0.05 to 1% by weight of the composition,
   wherein the composition has a viscosity of 1 to 100 mPas (cps).

10. An aqueous, foamable composition comprising:
    a) one or more anionic surfactants in an amount of 10 to 15% by weight of the composition,
    b) castor oil maleate in an amount of 0.1 to 1% by weight of the composition,
    c) glycerin in an amount of 0.5 to 6% by weight of the composition, and
    d) one or more amphoteric surfactants, wherein the one or more amphoteric surfactants comprises cocamidopropyl betaine, and wherein the cocamidopropyl betaine is present in an amount of 5.5% to 10% by weight of the composition.

11. The composition of claim 10, wherein the cocamidopropyl betaine is present in an amount of about 7% to 8% by weight of the composition.

12. The composition of claim 10, wherein glycerin is present in an amount of about 6% by weight of the composition.

13. The composition of claim 10, wherein the castor oil maleate is present in an amount of about 0.5% by weight of the composition.

14. The composition of claim 10, wherein the one or more anionic surfactants is sodium lauryl ether sulfate.

15. The composition of claim 10, wherein the one or more amphoteric surfactants comprises two different amphoteric surfactants.

16. The composition of claim 15, wherein the cocamidopropyl betaine is present in an amount of about 7% to 8% by weight of the composition.

17. The composition of claim 10, wherein the cocamidopropyl betaine is present in an amount of 5.5% to 6.5% by weight of the composition.

18. The composition of claim 10, wherein the cocamidopropyl betaine is present in an amount of about 6% by weight of the composition.

* * * * *